(12) United States Patent
Woodard et al.

(10) Patent No.: US 9,329,153 B2
(45) Date of Patent: May 3, 2016

(54) METHOD OF MAPPING ANOMALIES IN HOMOGENOUS MATERIAL

(71) Applicants: U.S.A. as represented by the Administrator of the National Aeronautics and Space Administration, Washington, DC (US); Marie Woodard

(72) Inventors: Stanley E. Woodard, Hampton, VA (US); Bryant D. Taylor, Smithfield, VA (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 384 days.

(21) Appl. No.: 13/796,626

(22) Filed: Mar. 12, 2013

(65) Prior Publication Data
US 2015/0260685 A1    Sep. 17, 2015

Related U.S. Application Data

(60) Provisional application No. 61/748,175, filed on Jan. 2, 2013.

(51) Int. Cl.
*G01N 27/82* (2006.01)
(52) U.S. Cl.
CPC ...................... *G01N 27/82* (2013.01)
(58) Field of Classification Search
CPC .......... G01B 7/34; G01B 15/06; G01B 15/08; G01N 9/24; G01N 27/02; G01N 27/82

USPC .......... 324/237–244, 345; 235/493, 449, 451, 235/492; 340/572.7, 572.1
See application file for complete search history.

(56) References Cited

U.S. PATENT DOCUMENTS 3,219,942 A    11/1965   Bell
3,412,359 A    11/1968   Schwyn et al.
(Continued)

OTHER PUBLICATIONS

John C. Butler, Anthony J. Vigliotti, Fred W. Verdi & Shawn M. Walsh, "Wireless, passive, resonant-circuit, inductively coupled, inductive strain sensor," Elsevier, Elsevier Science B.V., p. 63-86.
(Continued)

*Primary Examiner* — Arleen M Vazquez
*Assistant Examiner* — Robert P Alejnikov, Jr.
(74) *Attorney, Agent, or Firm* — Robin W. Edwards

(57) ABSTRACT

An electrical conductor and antenna are positioned in a fixed relationship to one another. Relative lateral movement is generated between the electrical conductor and a homogenous material while maintaining the electrical conductor at a fixed distance from the homogenous material. The antenna supplies a time-varying magnetic field that causes the electrical conductor to resonate and generate harmonic electric and magnetic field responses. Disruptions in at least one of the electric and magnetic field responses during this lateral movement are indicative of a lateral location of a subsurface anomaly. Next, relative out-of-plane movement is generated between the electrical conductor and the homogenous material in the vicinity of the anomaly's lateral location. Disruptions in at least one of the electric and magnetic field responses during this out-of-plane movement are indicative of a depth location of the subsurface anomaly. A recording of the disruptions provides a mapping of the anomaly.

21 Claims, 3 Drawing Sheets

(56) References Cited

U.S. PATENT DOCUMENTS

| | | | |
|---|---|---|---|
| 3,444,738 A | 5/1969 | Grangaard, Jr. |
| 3,755,803 A | 8/1973 | Cole et al. |
| 3,918,299 A | 11/1975 | Donnadieu |
| 3,975,706 A | 8/1976 | Kato |
| 4,021,705 A | 5/1977 | Lichtblau |
| 4,127,110 A | 11/1978 | Bullara |
| 4,302,965 A | 12/1981 | Johnson et al. |
| 4,510,484 A | 4/1985 | Snyder |
| 4,556,063 A | 12/1985 | Thompson et al. |
| 4,579,004 A | 4/1986 | Kalthoff et al. |
| 4,594,640 A | 6/1986 | Tatsumi |
| 4,626,311 A | 12/1986 | Taylor |
| 4,745,401 A | 5/1988 | Montean |
| 4,750,359 A | 6/1988 | Johnson et al. |
| 4,778,552 A | 10/1988 | Benge et al. |
| 4,912,407 A | 3/1990 | Gualtieri et al. |
| 4,929,896 A | 5/1990 | Lara |
| 4,977,786 A | 12/1990 | Davis |
| 5,049,704 A | 9/1991 | Matouschek |
| 5,075,600 A | 12/1991 | El-Hamamsy et al. |
| 5,094,409 A | 3/1992 | King et al. |
| 5,285,734 A | 2/1994 | MacPherson |
| 5,291,180 A | 3/1994 | Reeb |
| 5,389,097 A | 2/1995 | Bennett et al. |
| 5,420,757 A | 5/1995 | Eberhardt et al. |
| 5,423,206 A | 6/1995 | Hetzel |
| 5,423,334 A | 6/1995 | Jordan |
| 5,506,566 A | 4/1996 | Oldfield |
| 5,541,577 A | 7/1996 | Cooper et al. |
| 5,608,417 A | 3/1997 | De Vall |
| 5,675,319 A | 10/1997 | Rivenberg et al. |
| 5,689,263 A | 11/1997 | Dames |
| 5,705,981 A | 1/1998 | Goldman |
| 5,734,323 A | 3/1998 | Hermes et al. |
| 5,750,939 A | 5/1998 | Makinwa et al. |
| 5,832,772 A | 11/1998 | McEwan |
| 5,867,842 A | 2/1999 | Pinsley et al. |
| 5,873,840 A | 2/1999 | Neff |
| 5,881,310 A | 3/1999 | Airhart et al. |
| 5,892,425 A | 4/1999 | Kuhn et al. |
| 5,909,171 A | 6/1999 | Kyrtsos |
| 5,942,991 A | 8/1999 | Gaudreau et al. |
| 5,948,972 A * | 9/1999 | Samsavar et al. ............... 73/105 |
| 5,969,590 A | 10/1999 | Gutierrez |
| 5,975,250 A | 11/1999 | Brandmeier et al. |
| 6,012,162 A | 1/2000 | Bullat |
| 6,025,129 A | 2/2000 | Nova et al. |
| 6,025,725 A | 2/2000 | Gershenfeld et al. |
| 6,025,735 A | 2/2000 | Gardner et al. |
| 6,050,622 A | 4/2000 | Gustafson |
| 6,111,520 A | 8/2000 | Allen et al. |
| 6,147,606 A | 11/2000 | Duan |
| 6,164,132 A | 12/2000 | Matulek |
| 6,165,135 A | 12/2000 | Neff |
| 6,194,987 B1 | 2/2001 | Zhou et al. |
| 6,250,430 B1 | 6/2001 | Kyrtsos |
| 6,278,379 B1 | 8/2001 | Allen et al. |
| 6,282,942 B1 | 9/2001 | Husby |
| 6,304,083 B1 | 10/2001 | Owens |
| 6,304,169 B1 | 10/2001 | Blama et al. |
| 6,313,747 B2 | 11/2001 | Imaichi et al. |
| 6,317,048 B1 | 11/2001 | Bomya et al. |
| 6,335,690 B1 | 1/2002 | Konchin et al. |
| 6,348,391 B1 | 2/2002 | Fattaruso |
| 6,359,444 B1 | 3/2002 | Grimes |
| 6,384,721 B1 | 5/2002 | Paielli |
| 6,411,085 B1 * | 6/2002 | Siegel et al. ............... 324/240 |
| 6,412,977 B1 | 7/2002 | Black et al. |
| 6,439,508 B1 | 8/2002 | Taylor |
| 6,444,517 B1 | 9/2002 | Hsu et al. |
| 6,450,300 B1 | 9/2002 | Kramer |
| 6,463,798 B2 | 10/2002 | Niekerk et al. |
| 6,490,920 B1 | 12/2002 | Netzer |
| 6,498,325 B1 | 12/2002 | Akel et al. |
| 6,515,587 B2 | 2/2003 | Herbert |
| 6,517,483 B2 | 2/2003 | Park et al. |
| 6,532,834 B1 | 3/2003 | Pinto et al. |
| 6,546,795 B1 | 4/2003 | Dietz |
| 6,573,818 B1 | 6/2003 | Klemmer et al. |
| 6,611,188 B2 | 8/2003 | Yeo et al. |
| 6,615,954 B2 | 9/2003 | Wirth et al. |
| 6,639,402 B2 | 10/2003 | Grimes et al. |
| 6,642,720 B2 | 11/2003 | Maylotte et al. |
| 6,661,079 B1 | 12/2003 | Bikulcius |
| 6,662,642 B2 | 12/2003 | Breed et al. |
| 6,677,859 B1 | 1/2004 | Bensen |
| 6,696,953 B2 | 2/2004 | Qiu et al. |
| 6,738,697 B2 | 5/2004 | Breed |
| 6,741,169 B2 | 5/2004 | Magiawala et al. |
| 6,758,089 B2 | 7/2004 | Breed et al. |
| 6,834,251 B1 | 12/2004 | Fletcher |
| 6,838,970 B2 | 1/2005 | Basteres et al. |
| 6,850,162 B2 | 2/2005 | Cacioli et al. |
| 6,850,824 B2 | 2/2005 | Breed |
| 6,853,079 B1 | 2/2005 | Hopper et al. |
| 6,922,126 B1 | 7/2005 | Okamoto et al. |
| 6,963,281 B2 | 11/2005 | Buckley |
| 6,974,109 B1 | 12/2005 | Mezits et al. |
| 6,988,026 B2 | 1/2006 | Breed et al. |
| 6,995,669 B2 | 2/2006 | Morales |
| 7,017,195 B2 | 3/2006 | Buckman et al. |
| 7,034,672 B2 | 4/2006 | Dinello et al. |
| 7,047,807 B2 | 5/2006 | Woodard et al. |
| 7,050,017 B2 | 5/2006 | King et al. |
| 7,082,359 B2 | 7/2006 | Breed et al. |
| 7,082,833 B2 | 8/2006 | Heyman et al. |
| 7,086,593 B2 | 8/2006 | Woodard et al. |
| 7,089,099 B2 | 8/2006 | Shostak et al. |
| 7,103,460 B1 | 9/2006 | Breed |
| 7,134,785 B2 | 11/2006 | Takashima et al. |
| 7,135,973 B2 | 11/2006 | Kittel et al. |
| 7,159,774 B2 | 1/2007 | Woodard et al. |
| 7,161,476 B2 | 1/2007 | Hardman et al. |
| 7,194,912 B2 | 3/2007 | Oglesby et al. |
| 7,231,832 B2 | 6/2007 | Woodard et al. |
| 7,255,004 B2 | 8/2007 | Taylor et al. |
| 7,278,324 B2 | 10/2007 | Smits et al. |
| 7,506,541 B2 | 3/2009 | Woodard et al. |
| 7,683,797 B2 | 3/2010 | Woodard et al. |
| 7,711,509 B2 | 5/2010 | Woodard et al. |
| 7,814,786 B2 | 10/2010 | Woodard et al. |
| 7,902,815 B2 | 3/2011 | Woodard et al. |
| 8,042,739 B2 | 10/2011 | Woodard et al. |
| 2001/0001311 A1 | 5/2001 | Park et al. |
| 2002/0105325 A1 * | 8/2002 | Goldfine et al. ............... 324/242 |
| 2003/0020480 A1 | 1/2003 | Maylotte et al. |
| 2003/0082859 A1 | 5/2003 | Ichijo et al. |
| 2003/0214408 A1 | 11/2003 | Grajales et al. |
| 2004/0066296 A1 | 4/2004 | Atherton |
| 2004/0111790 A1 | 6/2004 | Dainese |
| 2004/0142603 A1 | 7/2004 | Walker |
| 2005/0011163 A1 | 1/2005 | Ehrensvard |
| 2005/0012615 A1 | 1/2005 | Piccoli et al. |
| 2005/0024180 A1 | 2/2005 | Handa |
| 2005/0122305 A1 | 6/2005 | Murao et al. |
| 2005/0149169 A1 | 7/2005 | Wang et al. |
| 2005/0156604 A1 | 7/2005 | Red'ko et al. |
| 2005/0164055 A1 | 7/2005 | Hasegawa et al. |
| 2005/0171703 A1 | 8/2005 | Goldfine et al. |
| 2006/0104330 A1 | 5/2006 | Ho Limb et al. |
| 2006/0191887 A1 | 8/2006 | Baer et al. |
| 2006/0195705 A1 | 8/2006 | Ehrensvard et al. |
| 2006/0243043 A1 | 11/2006 | Breed |
| 2006/0247868 A1 * | 11/2006 | Brandstrom ............... 702/35 |
| 2006/0250239 A1 | 11/2006 | Melton |
| 2007/0069895 A1 | 3/2007 | Koh |
| 2007/0113642 A1 | 5/2007 | Bonne et al. |
| 2007/0181683 A1 * | 8/2007 | Woodard et al. ............... 235/451 |
| 2007/0183110 A1 | 8/2007 | Woodard et al. |
| 2007/0210173 A1 | 9/2007 | Nagel |
| 2007/0285875 A1 | 12/2007 | Duff, Jr. |
| 2008/0186124 A1 | 8/2008 | Schaffer et al. |
| 2009/0072814 A1 * | 3/2009 | Woodard et al. ............... 324/173 |
| 2009/0109005 A1 | 4/2009 | Woodard et al. |

(56) References Cited

U.S. PATENT DOCUMENTS

| | | | |
|---|---|---|---|
| 2009/0143696 | A1 | 6/2009 | Najafi et al. |
| 2010/0109818 | A1 | 5/2010 | Woodard et al. |
| 2010/0207620 | A1* | 8/2010 | Gies .............................. 324/240 |
| 2010/0233821 | A1 | 9/2010 | Woodard et al. |
| 2011/0292969 | A1 | 12/2011 | Woodard |

OTHER PUBLICATIONS

K.G. Ong, C.A. Grimes, C.L. Robbins & R.S. Singh, "Design and application of a wireless, passive, resonant-circuit environmental monitoring sensor," Elsevier, Elsevier Science B.V., p. 33-43.

Keat Ghee Ong & Craig A. Grimes, "A resonant printed-circuit sensor for remote query monitoring of environmental paramters," Smart Materials Struct. 9 (2000), p. 421-426.

Stanley E. Woodard et al., "Magnetic Field Response Measurement Acquisition System," NASA TM 2005-213518, NASA, (Feb. 1, 2005).

Stanley E. Woodard and Bryant D. Taylor, "Measurement of Multiple Unrelated Physical Quantities Using a Single Magnetic Field Response Sensor," Measurement Science and Technology (UK), (vol. 18), (Issue 200), (pp. 1603-1613).

G. Schimetta, F. Dollinger, and R. Weigel, "A Wireless Pressure-Measurement System Using a SAW Hybrid Sensor", IEEE Transactions on Microwave Theory and Techniques, vol. 48, No. 12, Dec. 2000.

G. Schimetta, F. Dollinger, G. Scholl, and R. Weigel, "Wireless Pressure and Temperature Measurement Using a SAW Hybrid Sensor". 2000 IEEE Ultrasonics Symposium, pp. 445-448.

Ya Wang, Yi Jia, Qiushui Chen, and Yanyun Wang, "A Passive Wireless Temperature Sensor for Harsh Environment Applications", Sensors 2008, 8,7982-7995.

Lorrain, P., and Corson, D.R., "Electromagnetic Field and Waves," W.H. Freeman and Company, 1970, San Francisco, CA, pp. 91-128, 292-373 and 471-481.

Woodard, S.E., "Functional Electrical Sensors as Single Component Electrically Open Circuits Having no Electrical Connections," IEEE Transactions on Instrumentation and Measurement, vol. 59, No. 12, Dec. 2010.

Woodard, S.E., Oglesby, D.M., Taylor, B.D., and Shams, Q.A., "Chemical Detection Using Electrically Open Circuits Having no Electrical Connections," the 6th IEEE Conference on Sensors, Lecce, Italy, IEEE 6339, Oct. 2008.

Woodard, S.E., Title of Investigation: Planetary Probes with Sensing Skins/Blankets of Open-Circuit Sensors Proposal, NASA Langley Research Center, 2009.

Woodard, S.E., "Spectroscopy using Electric Permittivity, Magnetic Permeability and Electrical Conductivity Spatial Profiles," NASA Langley Research Center, 2009.

* cited by examiner

METHOD OF MAPPING ANOMALIES IN HOMOGENOUS MATERIAL

Pursuant to 35 U.S.C. §119, the benefit of priority from provisional application 61/748,175, with a filing date of Jan. 2, 2013, is claimed for this non-provisional application.

ORIGIN OF THE INVENTION

This invention was made in part by an employee of the United States Government and may be manufactured and used by or for the Government of the United States of America for governmental purposes without the payment of any royalties thereon or therefor.

BACKGROUND OF THE INVENTION

1. Field of the Invention

This invention relates to methods for locating anomalies in materials. More specifically, the invention is a wireless method for mapping anomalies in homogenous materials.

2. Description of the Related Art

Inspections of materials for anomalies (e.g., faults, degradation, weakness, damage, etc.) embedded therein can provide critical structural health information for vehicles (e.g., aircraft, undersea vehicles, trucks and automobiles, etc.) and static structures (e.g., buildings, bridges, etc.). Ideally, such inspections are carried out non-invasively in order to preserve material integrity. Typically, such inspections involve interpretation of what is visible on a material surface or utilization of penetrating-ray scanner technology such as an x-ray. However, using a surface analysis to predict subsurface anomalies is frequently nothing more than an educated guess that can prove catastrophic if an embedded anomaly is missed or that can involve expensive and unnecessary repair/replacement when a false positive guess is made. The use of x-ray scanners is not always possible due to cost of the equipment, feasibility of getting the equipment in place or getting the material to the equipment, and may not always provide enough information regarding an anomaly's three-dimensional location in a material.

SUMMARY OF THE INVENTION

Accordingly it is an object of the present invention to provide a method of mapping anomalies embedded in a material.

Another object of the present invention is to provide a method of mapping lateral and depth locations of anomalies embedded within a material.

Still another object of the present invention is to provide a non-invasive method of mapping anomalies embedded in a material.

Other objects and advantages of the present invention will become more obvious hereinafter in the specification and drawings.

In accordance with the present invention, a method is provided for mapping anomalies in a homogenous material. The method uses an electrical conductor having first and second ends and shaped between the first and second ends for storage of an electric field and a magnetic field. The first and second ends remain electrically unconnected such that the electrical conductor is maintained as an unconnected single-component, open-circuit having inductance and capacitance. In the presence of a time-varying magnetic field, the electrical conductor resonates to generate harmonic electric and magnetic field responses, each of which has a frequency, amplitude and bandwidth associated therewith. The method also uses a magnetic field response recorder having an antenna for wireless transmission of the time-varying magnetic field to the electrical conductor and for wireless detection of the frequency, amplitude and bandwidth associated with at least one of the electric and magnetic field responses. The electrical conductor and antenna are positioned in a fixed relationship to one another. Relative lateral movement is generated between the electrical conductor and a homogenous material while maintaining the electrical conductor at a fixed distance from the homogenous material. Disruptions in at least one of the electric and magnetic field responses during this lateral movement are indicative of a lateral-location of an anomaly in the homogenous material at a region thereof. Next, relative out-of-plane movement is generated between the electrical conductor and the homogenous material in the vicinity of the anomaly's lateral location. Disruptions in at least one of the electric and magnetic field responses during this out-of-plane movement are indicative of a depth location of the anomaly in the homogenous material. At least one of the electric and magnetic field responses during the lateral and out-of-plane movements are recorded with the anomaly being mapped by the response disruptions.

DETAILED DESCRIPTION OF THE INVENTION

Figure 1:
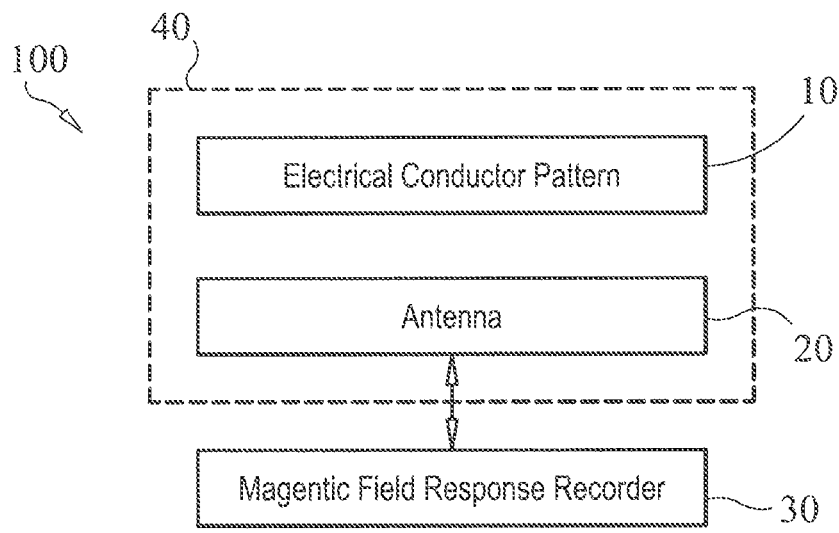
FIG. 1 is a schematic view of a wireless system used in the mapping of anomalies embedded in a material in accordance with the present invention.

Referring now to the drawings and more particularly to FIG. 1, a wireless system for mapping anomalies in a material in accordance with an embodiment of the present invention is shown and is referenced generally by numeral 100. The illustrated system 100 is presented as an exemplary embodiment as there will be many possible embodiments that can be constructed based on the basic principles of the present invention without departing from the scope thereof. In the illustrated embodiment, system 100 includes a pattern 10 of electrically conductive material, an antenna 20 spaced apart from pattern 10 and in a fixed relationship thereto, and a magnetic field response recorder 30 coupled to antenna 20.

Electrical conductor pattern 10 is any electrical conductor (e.g., wire, run, thin-film trace, etc.) that can be shaped to form an open-circuit pattern that can store an electric field and a magnetic field. Pattern 10 is a single-component open-circuit element with no electrical, connections being made thereto. The term "open-circuit pattern" as used herein means that the conductor has two ends that are/remain electrically unconnected so that the resulting conductor pattern is a single-component, electrical open-circuit having inductance and capacitance attributes.

Pattern 10 can be a stand-alone electrically-conductive run. Pattern 10 can also be made from an electrically-conductive run or thin-film trace that can be deposited directly onto or embedded within an optional substrate material 40 (referenced by dashed lines to indicate the optional nature thereof) that is electrically insulating and non-conductive. To facilitate the fixed and spaced-apart relationship between pattern 10 and antenna 20, substrate 40 can also be used to support antenna 20 as illustrated in FIG. 1. The particular choice of the substrate/embedding material can vary without departing from the scope of the present invention. Although not a requirement of the present invention, the surface on which pattern 10 is deposited is typically a planar surface such that pattern 10 lies in a plane or is planar. Techniques used to deposit pattern 10 directly onto substrate 40 can be any conventional metal-conductor deposition process to include thin-film fabrication techniques. Pattern 10 can be constructed to have a uniform or non-uniform width, and/or uniform or non-uniform spacing between adjacent portions of the pattern's runs/traces.

Figure 2:
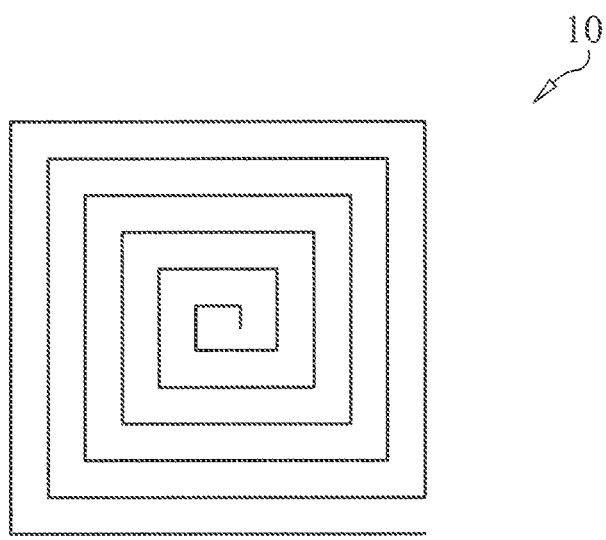
FIG. 2 is an isolated plan view of an electrical conductor shaped in a spiral for use in the wireless system in accordance with an embodiment of the present invention.

The basic features of pattern 10 and the principles of operation for system 100 will be explained for a spiral-shaped conductor pattern as illustrated in FIG. 2. However, it is to be understood that the present invention could be practiced using other geometrically-patterned conductors provided the pattern has the attributes described herein. The basic features of a spiral-shaped conductor that can function as pattern 10 are described in detail in U.S. Patent Publication No. 2007/0181683, the contents of which are hereby incorporated by reference. For purpose of a complete description of the present invention, the relevant portions of this publication will be repeated herein.

As is well known and accepted in the art, a spiral inductor is ideally constructed/configured to minimize parasitic capacitance so as not to influence other electrical components that will be electrically coupled thereto. This is typically achieved by increasing the spacing between adjacent conductive portions or runs of the conductive spiral pattern. However, in the present invention, pattern 10 exploits parasitic capacitance. The capacitance of pattern 10 is operatively coupled with the pattern's inductance such that magnetic and electrical energy can be stored and exchanged by the pattern thereby creating a damped simple harmonic resonator. Since other geometric patterns of a conductor could also provide such a magnetic/electrical, energy storage and exchange, it is to be understood that the present invention could be realized using any such geometrically-patterned conductor and is not limited to a spiral-shaped pattern.

The amount of inductance along any portion of a conductive run of pattern 10 is directly related to the length thereof and inversely related to the width thereof. The amount of capacitance between portions of adjacent conductive runs of pattern 10 is directly related to the length by which the runs overlap each other and is inversely related to the spacing between the adjacent conductive runs. The amount of resistance along any portion of a conductive run of pattern 10 is directly related to the length and inversely related to the width of the portion. Total capacitance, total inductance and total resistance for a spiral pattern are determined simply by adding the effective contributions due to individual portions of the pattern. For example, the effective inductance contribution of a trace portion is the resultant change in the total inductance of pattern 10 due to the changes in the pattern's distributed self-inductance and distributed mutual inductance due to the addition of the trace. The effective capacitance contribution of a trace portion is the resulting change in the capacitance or pattern 10 due to the addition of the trace portion as a result of the charge in the portion creating electric fields with the charges in other parts of pattern 10 thus increasing the total distributed capacitance. The geometries of the various portions of the conductive runs of the pattern can be used to define the pattern's resonant frequency.

Pattern 10 with its distributed inductance operatively coupled to its distributed capacitance defines a magnetic field response sensor. In the presence of a time-varying magnetic field, pattern 10 electrically oscillates at a resonant frequency that is dependent upon the capacitance, inductance and resistance of pattern 10. This oscillation occurs as the energy in the magnetic field along the length of pattern 10 is harmonically transferred to the electric field between parallel portions of pattern 10. That is, when excited by a time-varying magnetic field, pattern 10 resonates a harmonic electric field and a harmonic magnetic field with each field being defined by a frequency, amplitude, and bandwidth.

The application of an oscillating magnetic field to pattern 10 as well as the reading and recording of the induced harmonic, response at a resonant frequency can be accomplished by a magnetic field response recorder. The operating principles and construction details of such a recorder are provided in U.S. Pat. Nos. 7,085,593 and 7,159,774, the contents of which are hereby incorporated by reference. Briefly, magnetic field response recorder 30 includes a processor and a broadband radio frequency (RF) antenna capable of transmitting and receiving RF energy. In the present invention, the antenna utilized by magnetic field response recorder 30 is antenna 20. Accordingly, it is to be understood, that pattern 10 and antenna 20 (e.g., coupled together using substrate 40) could be a separate assembly that is then operatively coupled to the processing/recording portion of recorder 30, or antenna 20 could be part of recorder 30 without departing from the scope of the present invention.

The processor in recorder 30 includes algorithms embodied in software for controlling antenna 20 and for recording the RF signals received (by antenna 20) from the magnetic field response sensor defined by pattern 10. Such signal recordation can come in the form of data storage, data display, data printouts, and/or combinations thereof without departing from the scope of the present invention.

On the transmission side, magnetic field response recorder 30 modulates an input signal that is then supplied to antenna 20 so that antenna 20 produces either a broadband time-varying magnetic field or a single harmonic field. Then, on the reception side, antenna 20 receives harmonic electric and magnetic field responses produced by pattern 10. Antenna 20 can be realized by two separate antennas (i.e., one for transmission, one for reception) or a single antenna that is switched between transmission and reception.

In the illustrated embodiment, pattern 10 lies in a two-dimensional plane and antenna 20 lies in a plane that is substantially parallel to that of pattern 10 and in a fixed relationship thereto. However, the present invention is not so limited as pattern 10 could occupy three-dimensional space.

In operation, when pattern 10 is exposed to a time-varying magnetic field (e.g., as generated by recorder 30, a moving magnet, or any other source/method that generates an oscillating magnetic field), pattern 10 resonates harmonic electric and magnetic fields. The generated magnetic field is generally spatially larger than the generated electric field. The monitoring and recording of the electric and magnetic field responses serves as the basis for mapping embedded or subsurface anomalies in a material.

For purposes of the present invention, the material to be monitored/mapped is a homogenous material that can be monolithic or a layer of a laminate structure. The material's homogeneity provides for the establishment of baseline electric and magnetic field responses that can be compared to subsequent electric and magnetic field responses. That is, changes or disruptions in the subsequent electric and magnetic field responses (as compared to the baseline responses) are indicative of anomalies to be mapped.

Figure 3A:
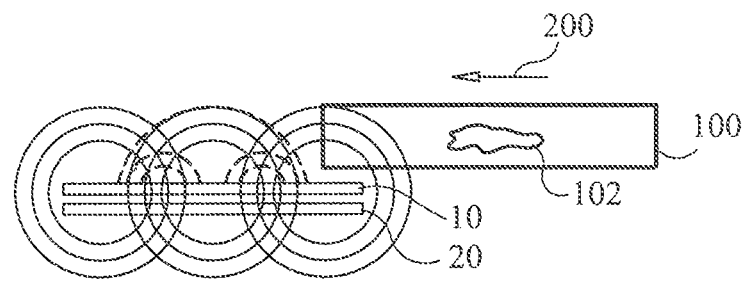
FIGS. 3A, 3B, 3C, 3D and 3E depict a material with an embedded anomaly at a number of lateral positions in relation to the electric and magnetic field responses of an electrical conductor pattern in accordance with an embodiment of the mapping method of the present invention.
Figure 3B:
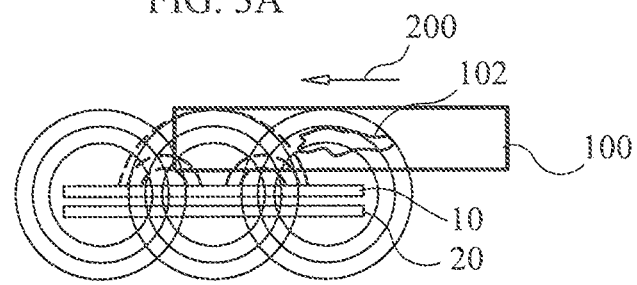
Figure 3C:
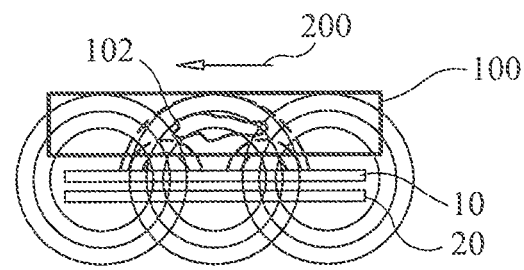
Figure 3D:
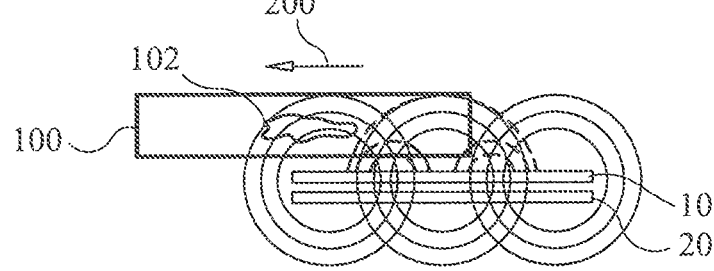
Figure 3E:
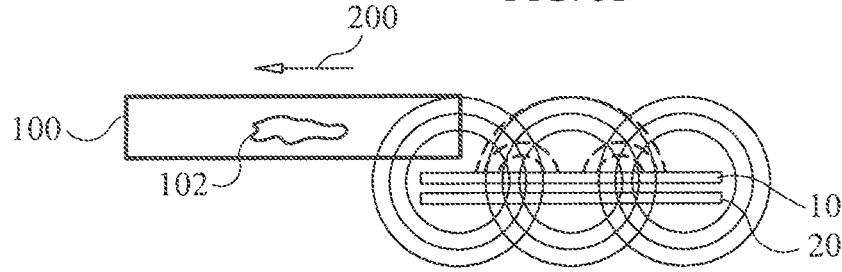

An example of the mapping method of the present invention will now be explained with reference to the diagram sequences illustrated in FIGS. 3 and 4. In general, the sequence illustrated in FIGS. 3A-3E is used to locate/map the lateral location of a subsurface anomaly, while the sequence illustrated in FIGS. 4A-4C is used to locate/map the depth location of the detected subsurface anomaly. In each of the figures, pattern 10 is assumed to be a planar spiral electrical conductor as described above, and antenna 20 is assumed to be producing a time-varying magnetic field. Accordingly, pattern 10 resonates harmonic electric and magnetic fields where the electric field lines are represented by dashed lines and the magnetic field lines are represented by solid lines. For clarity of illustration, the structure used to fix pattern 10 and antenna 20 in their relative positions has been omitted as has the coupling of magnetic field response recorder 30 to antenna 20. Further, in each of the figures, a homogenous material 100 is assumed to have a subsurface anomaly 102 embedded therein. The nature and/or source of anomaly 102 are not limitations of the present invention.

In accordance with the present invention, two types of relative motion between material 100 and pattern 10/antenna 20 are used. Briefly, relative lateral motion is used to locate/map the lateral location of anomaly 102, while relative out-of-plane motion is used to locate/map the depth location of anomaly 102. Referring first to FIGS. 3A-3E, the lateral motion will be described. It is to be understood that the relative lateral motion between material 100 and pattern 10/antenna 20 (indicated by arrow 200) can be generated by moving just material 100, just pattern 10/antenna 20, or both, without departing from the scope of the present invention. During such lateral motion, antenna 10 is maintained at a fixed distance from (a surface) of material 100. In cases where the surface of material 100 is planar and pattern 10 is a planar spiral, pattern 10 and the surface of material 100 will remain parallel to one another during the lateral motion portion of the present method.

Both electric and magnetic field responses of pattern 10 are illustrated in FIGS. 3 and 4. However, it is to be understood that just the electric field response, just the magnetic field response, or both, can be used during the locating/mapping of subsurface anomalies. The choice of response(s) used can be predicated on the attributes of material 100 and/or the types of anomaly 102 of interest. Further, since the magnetic field response generally extends further from pattern 10 than the electric field response, the proximity of the material's anomaly to pattern 10 could determine which type of response is used for anomaly mapping in the present invention.

As mentioned above, prior to inspection of material 100, the above-described system 10 (FIG. 1) would be calibrated with baseline electric and/or magnetic field responses for material 100 having no anomalies. Accordingly, it is assumed the sequences in FIGS. 3 and 4 depict a subsequent inspection time when anomaly 102 is present. During a subsequent inspection, FIG. 3A depicts material 100 (but not anomaly 102) entering the electrical and magnetic field responses of pattern 10. Since anomaly 102 has not entered the response region, the response(s) will match that of the baseline responses use during system calibration. However, as relative lateral motion 200 causes anomaly 102 to move through the response region as illustrated in FIGS. 3B-3D, disruptions (i.e., changes in frequency, bandwidth and/or amplitude) in the response(s) will occur as compared to the baseline responses. The recording of these disruptions (e.g., by recorder 30) as a function of lateral position of material 100 provides a lateral location mapping of anomaly 102. The endpoint of the lateral location is readily detected once anomaly 102 has passed out of the response region as depicted in FIG. 3E.

Figure 4A:
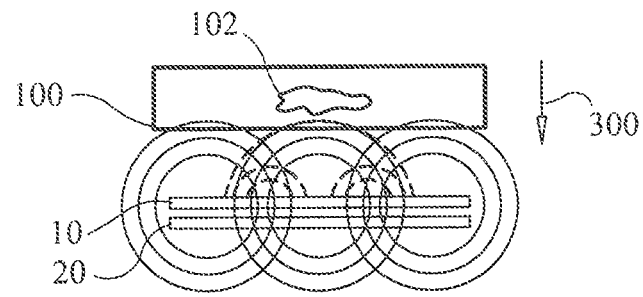
FIGS. 4A, 4B and 4C depict the material with the embedded anomaly at a number of out-of-plane positions in relation to the electric and magnetic field responses of the electrical conductor pattern in accordance with an embodiment of the mapping method of the present invention.
Figure 4B:
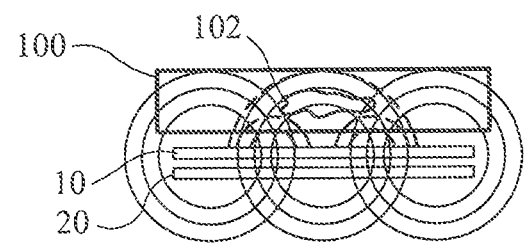
Figure 4C:
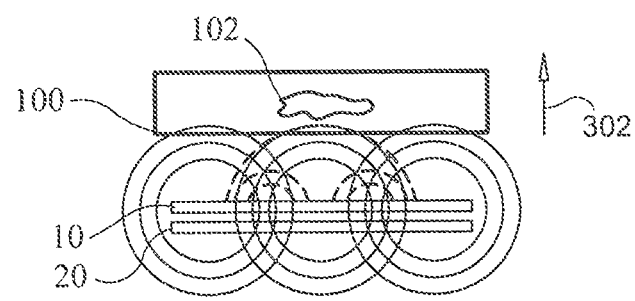

The present invention is next utilized to map the depth location of anomaly 102 as illustrated by the sequence in FIG. 4. Briefly, relative out-of-plane motion between material 100 and pattern 10/antenna 20 is indicated by either arrow 300 (FIG. 4A) or arrow 302 (FIG. 4C). In cases where the surface of material 100 is planar and pattern 10 is a planar spiral, out-of-plane motion 300/302 is defined as being substantially perpendicular to the surface of material 100. As with relative lateral motion 200, the out-of-plane motion can result from moving just material 100, just pattern 10/antenna 20, or both.

The out-of-plane motion is introduced in the vicinity of anomaly 102. That is, the present invention uses the above-described lateral motion to map a lateral location of anomaly 102, and then applies out-of-plane motion in the vicinity of the mapped lateral location to map the depth location of anomaly 102. Specifically, FIG. 4A depicts material 100 experiencing relative out-of-plane motion 300 where a surface of material 100 and pattern 10 are getting closer to one another in the vicinity of anomaly 102 but anomaly 102 has not entered the response region of pattern 10. FIG. 4B depicts anomaly 102 in the response region, while FIG. 4C depicts anomaly 102 after it has once again moved out of the response region due to out-of-plane motion 302 that, is in the opposite direction of motion 300. As with the lateral motion mapping, the response(s) of pattern 10 will be disrupted during the time that anomaly 102 is present therein. The recording of these disruptions (e.g., by recorder 30) provides a depth location mapping of anomaly 102.

The advantages of the present invention are numerous. Subsurface anomaly mapping is accomplished in a noninvasive fashion using equipment that is relatively inexpensive. The (electrical, conductor) pattern, and antenna combination can be readily incorporated into a hand-held unit thereby allowing the present method to map subsurface anomalies in a variety of hard-to-reach locales of a structure. The pattern/antenna combination could, also be relatively large and incorporated into a vehicle thereby turning the vehicle into a large anomaly sensing/mapping system. The method can be used to inspect a variety of types of materials thereby increasing its utility for a myriad of applications.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A method of mapping anomalies in a homogenous material, comprising the steps of:
    providing an electrical conductor having first and second ends and shaped between said first and second ends for storage of an electric field and a magnetic field, said first and second ends remaining electrically unconnected such that said electrical conductor is maintained as an unconnected single-component open-circuit having inductance and capacitance wherein, in the presence of a time-varying magnetic field, said electrical conductor resonates to generate harmonic electric and magnetic field responses, each of which has a frequency, amplitude and bandwidth associated therewith;

providing a magnetic field response recorder having an antenna for wirelessly transmitting said time-varying magnetic field to said electrical conductor and for wirelessly detecting said frequency, amplitude and bandwidth associated with at least one of said electric and magnetic field responses;

positioning said electrical conductor and said antenna in a fixed relationship to one another;

establishing, at a calibration time, baseline electric and magnetic field responses for a homogeneous material known to be free of anomalies;

generating, at an inspection time that is subsequent to said calibration time, relative lateral movement between said electrical conductor and the homogenous material while maintaining said electrical conductor at a fixed distance from the homogenous material, wherein changes between at least one of said electric and magnetic field responses during said lateral movement and said baseline electric and magnetic field responses are indicative of a lateral location of an anomaly in the homogenous material at a region thereof;

generating, at said inspection time, relative out-of-plane movement between said electrical conductor and the homogenous material in the vicinity of said lateral location wherein changes between at least one of said electric and magnetic field responses during said out-of-plane movement and said baseline electric and magnetic field responses are indicative of a depth location of the anomaly in the homogenous material; and recording said changes during said lateral movement and said changes during said out-of-plane movement wherein the anomaly is mapped thereby.

2. A method according to claim 1, wherein said electrical conductor and a surface of the homogenous material remain substantially parallel to one another during said lateral movement.

3. A method according to claim 1, wherein said out-of-plane movement is substantially perpendicular to a surface of the homogenous material.

4. A method according to claim 1, wherein said lateral movement is generated by moving only said electrical conductor and said antenna.

5. A method according to claim 1, wherein said out-of-plane movement is generated by moving only said electrical conductor and said antenna.

6. A method according to claim 1, wherein said lateral movement is generated by moving only the homogenous material.

7. A method according to claim 1, wherein said out-of-plane movement is generated by moving only the homogenous material.

8. A method of mapping anomalies in a homogenous material, comprising the steps of:

providing an electrical conductor having first and second ends and shaped to form a spiral between said first and second ends for storage of an electric field and a magnetic field, said spiral lying in a plane, said first and second ends remaining electrically unconnected such that said electrical conductor is maintained as an unconnected single-component open-circuit having inductance and capacitance wherein, in the presence of a time-varying magnetic field, said electrical conductor resonates to generate harmonic electric and magnetic field responses, each of which has a frequency, amplitude and bandwidth associated therewith;

providing a magnetic field response recorder having an antenna for wirelessly transmitting said time-varying magnetic field to said electrical conductor and for wirelessly detecting said frequency, amplitude and bandwidth associated with at least one of said electric and magnetic field responses;

positioning said electrical conductor and said antenna in a fixed spaced-apart relationship to one another;

establishing, at a calibration time, baseline electric and magnetic field responses for a homogeneous material known to be free of anomalies;

generating, at an inspection time that is subsequent to said calibration time, relative lateral movement between said electrical conductor and a surface of the homogenous material while maintaining said electrical conductor at a fixed distance from the surface of the homogenous material, wherein changes between at least one of said electric and magnetic field responses during said lateral movement and said baseline electric and magnetic field responses are indicative of a lateral location of an anomaly in the homogenous material at a region thereof;

generating, at said inspection time, relative out-of-plane movement between said electrical conductor and the homogenous material in the vicinity of said lateral location wherein changes between at least one of said electric and magnetic field responses during said out-of-plane movement and said baseline electric and magnetic field responses are indicative of a depth location of the anomaly in the homogenous material; and recording said changes during said lateral movement and said changes during said out-of-plane movement wherein the anomaly is mapped thereby.

9. A method according to claim 8, wherein said electrical conductor and the surface of the homogenous material remain substantially parallel to one another during said lateral movement.

10. A method according to claim 8, wherein said out-of-plane movement is substantially perpendicular to the surface of the homogenous material.

11. A method according to claim 8, wherein said lateral movement is generated by moving only said electrical conductor and said antenna.

12. A method according to claim 8, wherein said out-of-plane movement is generated by moving only said electrical conductor and said antenna.

13. A method according to claim 8, wherein said lateral movement is generated by moving only the homogenous material.

14. A method according to claim 8, wherein said out-of-plane movement is generated by moving only the homogenous material.

15. A method of mapping anomalies in a homogenous material, comprising the steps of:

providing an antenna in a fixed spaced-apart relationship with an electrical conductor, said electrical conductor having first and second ends and shaped to form a spiral between said first and second ends for storage of an electric field and a magnetic field, said first and second ends remaining electrically unconnected such that said electrical conductor is maintained as an unconnected single-component open-circuit having inductance and capacitance;

coupling a magnetic field response recorder to said antenna;

establishing, at a calibration time, baseline electric and magnetic field responses for a homogeneous material known to be free of anomalies;

operating said magnetic field response recorder such that (i) said antenna wirelessly transmits a time-varying magnetic field to said electrical conductor wherein, in the presence of said time-varying magnetic field, said electrical conductor resonates to generate harmonic electric and magnetic field responses, each of which has a frequency, amplitude and bandwidth associated therewith, and (ii) said antenna wirelessly detects said frequency, amplitude and bandwidth associated with at least one of said electric and magnetic field responses;

generating, at an inspection time that is subsequent to said calibration time, relative lateral movement between said electrical conductor and the homogenous material while maintaining said electrical conductor at a fixed distance from the homogenous material, wherein changes between at least one of said electric and magnetic field responses during said lateral movement and said baseline electric and magnetic field responses are indicative of a lateral location of an anomaly in the homogenous material at a region thereof;

generating relative out-of-plane movement between said electrical conductor and the homogenous material in the vicinity of said lateral location wherein changes between at least one of said electric and magnetic field responses during said out-of-pane movement and said baseline electric and magnetic field responses are indicative of a depth location of the anomaly in the homogenous material; and recording said changes during said lateral movement and said changes during said out-of-plane movement wherein the anomaly is mapped thereby.

16. A method according to claim 15, wherein said electrical conductor and a surface of the homogenous material remain substantially parallel to one another during said lateral movement.

17. A method according to claim 15, wherein said out-of-plane movement is substantially perpendicular to the surface of the homogenous material.

18. A method according to claim 15, wherein said lateral movement is generated by moving only said electrical conductor and said antenna.

19. A method according to claim 15, wherein said out-of-plane movement is generated by moving only said electrical conductor and said antenna.

20. A method according to claim 15, wherein said lateral movement is generated by moving only the homogenous material.

21. A method according to claim 15, wherein said out-of-plane movement is generated by moving only the homogenous material.

* * * * *